United States Patent [19]

Stormbom

[11] Patent Number: 5,607,564
[45] Date of Patent: Mar. 4, 1997

[54] METHOD OF PRODUCING A MICROPOROUS, GAS PERMEABLE ELECTRODE STRUCTURE AND A MICROPOROUS, GAS PERMEABLE ELECTRODE STRUCTURE

[75] Inventor: Lars Stormbom, Vantaa, Finland

[73] Assignee: Vaisala OY, Helsinki, Finland

[21] Appl. No.: 371,128

[22] Filed: Jan. 11, 1995

[30] Foreign Application Priority Data

Jan. 18, 1994 [FI] Finland ................................ 940240

[51] Int. Cl.$^6$ ........................................... G01N 27/26
[52] U.S. Cl. .................. 204/284; 204/290 R; 204/292; 204/192.15; 427/248.1; 427/250; 427/566; 427/567; 427/597; 427/404; 427/405; 427/419.2
[58] Field of Search .................. 204/290 R, 284, 204/292, 192.15; 429/40; 427/248.1, 250, 566, 567, 562, 586, 596, 597, 404, 405, 419.2

[56] References Cited

U.S. PATENT DOCUMENTS

| | | | |
|---|---|---|---|
| 4,500,395 | 2/1985 | Nakamura | 204/284 |
| 4,612,100 | 9/1986 | Edeling et al. | 204/192.15 |
| 5,035,790 | 7/1991 | Morimoto et al. | 207/292 |
| 5,104,695 | 4/1992 | Greer et al. | 427/250 |

*Primary Examiner*—Bruce F. Bell
*Attorney, Agent, or Firm*—Birch, Stewart, Kolasch & Birch, LLP

[57] ABSTRACT

The invention relates to a method of producing a microporous, gas permeable electrode structure, and to a corresponding electrode structure. According to the method, on a substrate (2) by means of a vacuum evaporation process is formed a first microporous electrode layer (4) using an angle (α) between the substrate (2) and the evaporation source (1) smaller than 90°. According to the invention, on the first microporous layer (4) is formed another microporous layer (5) of a precious metal using essentially the same evaporation angle (α) as in the fabrication step of the first microporous layer (4).

16 Claims, 1 Drawing Sheet

METHOD OF PRODUCING A MICROPOROUS, GAS PERMEABLE ELECTRODE STRUCTURE AND A MICROPOROUS, GAS PERMEABLE ELECTRODE STRUCTURE

The invention is related to a method for producing a microporous, gas permeable electrode structure.

The invention also concerns a microporous, gas permeable electrode structure.

Capacitive gas and humidity sensors conventionally employ a gas permeable, yet electrically conductive electrode. The electrode can be produced using a variety of different methods. For instance, some metals exhibit strong tensile stress during vacuum deposition that results in microcracks. Such electrode structures are described in, e.g., U.S. Pat. No. 5,075,816. However, these methods easily leave residual stresses in the electrode structure that are detrimental to the stability of the sensor. Another method is to form the electrode starting from an extremely thin layer of gold or platinum. This method is hampered by the poor adhesion of the precious metal to the underlying layer and the difficult controllability of the deposition process.

A method widely employed in the art is the formation of the electrode by a silk-screening process and subsequent sintering of conductive paste on a substrate. Due to the high sintering process temperature, this method is hampered by setting specific requirements on the other materials used in the sensor structure and resulting in a thick electrode.

An essential property characterizing the electrode is the mutual spacing of pores or microcracks from each other as this specification directly affects the response time of the sensor. Typically, the goal is to make the electrode such that the mutual distance of the pores is smaller than the thickness of the active material layer in the sensor structure, whereby the limiting factor to the sensor response time will be the thickness of the active material layer.

Furthermore, if the pore size can be controlled so that, e.g., large molecules cannot pass through the pores, this may significantly improve the selectivity of the sensor. However, this may in practice require a relatively small pore size (smaller than 30 nm).

Vacuum evaporation can achieve porous metal films by changing the angle between the metal source and the surface to be vacuum coated with the metal from normal to a smaller oblique angle (cf. Katsuri L. Chopra, "Thin Film Phenomena", pp. 176–177). This approach offers a controlled method of producing pores of desired size. To achieve a sufficiently good adhesion, the electrode structure must generally be made from a slightly oxidizing material. Such materials typically include Cr, Ti and Ni, as well as alloys thereof. The above-described electrode structure has the drawback of slow oxidation of the metal after completion of electrode fabrication, frequently resulting in plugging of the pores.

SUMMARY OF THE INVENTION

It is an object of the present invention to overcome the drawbacks of the above-described techniques and to achieve an entirely novel method of producing a microporous, gas permeable electrode and to provide such a microporous, gas permeable electrode.

The invention is based on using a small-angle vacuum evaporation process for forming an oxidation-resisting layer of (non-oxidizing) precious material (metal) onto said (self-oxidizing) layer of good adherence to the substrate using the same small-angle vacuum evaporation process as is used in the above-described fashion for making said self-oxidizing layer.

More specifically, the method according to the invention is characterized by forming on a substrate's surface by means of a vacuum evaporation process, a first microporous layer using an evaporation angle (α) between the substrate's surface and an evaporation source that is smaller than 90°, and forming on the first microporous layer, by means of a vacuum evaporation process, a second microporous layer that is made of a precious metal using essentially the same evaporation angle (α) between the substrate's surface and the evaporation source as used in forming the first microporous layer.

Furthermore, the electrode structure according to the invention is characterized by a substrate having formed thereon a first microporous gas permeable electrode layer, and formed on said first microporous gas permeable electrode layer a second microporous gas permeable layer made of a precious metal.

The invention offers significant benefits.

The electrode structure can be produced in a fully controlled fashion to a desired degree of gas permeability without any aging problems involved. Good adherence of the microporous layer to the underlying substrate is attained. Owing to the freedom from aging problems, the microporous electrode structure is capable of offering a "molecular" filter suited to, e.g., preventing the access of high-molecular-weight solvent molecules to the interior of the electrode structure.

BRIEF DESCRIPTION OF THE DRAWINGS

In the following, the invention will be examined in more detail by means of exemplifying embodiments with reference to the attached drawings, in which.

DETAILED DESCRIPTION OF THE INVENTION

Figure 1:
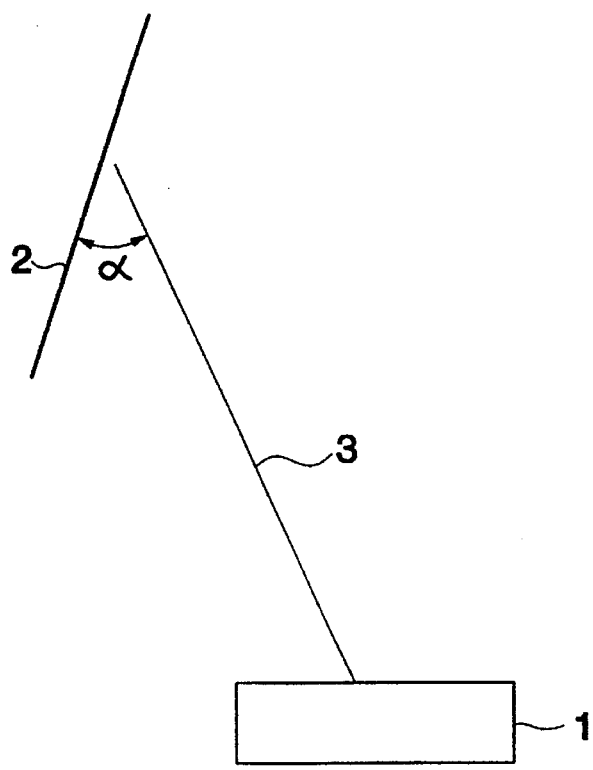
FIG. 1 is a diagrammatic side view of the deposition process arrangement according to the invention.

With reference to FIG. 1, the microporous metal film is attained by adjusting the angle α between the surface 2 to be metallized and the source 1 evaporating the metal to a value in the range 5°–30°. By altering the angle, the porosity and pore size of the metal film can be modified so that a small value of the angle α gives an extremely porous layer of large pore size, while a larger value of the angle α results in a less permeable layer of smaller pores.

Figure 2:
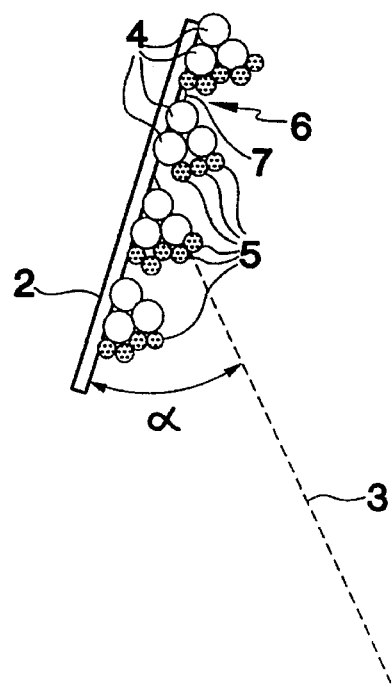
FIG. 2 is a detail of the process arrangement shown in FIG. 1.

With reference to FIG. 2, good adherence is attained by first vacuum evaporating a layer of a slightly self-oxidizing metal 4 (such as Cr, Ni or Ti) to a thickness of 10–300 nm. The plugging of pores 6 through oxidation is prevented by subsequently vacuum evaporating from the same angle a precious metal layer 5 (of Au, Pt or Pd) to a thickness of 10–300 nm. Typically, the total thickness of these layers 4 and 5 is in the range 30–400 nm.

Advantageously, the pore size 7 (minimum diameter of the pores) is smaller than 30 nm, whereby a filtering effect against high-molecular-weight molecules is achieved.

I claim:

1. A method of producing a microporous, gas permeable electrode structure, which method comprises:

forming on a substrate's surface, by means of a vacuum evaporation process, a first microporous layer using an evaporation angle ($\alpha$) between the substrate's surface and an evaporation source that is smaller than 90°, and forming on the first microporous layer, by means of a vacuum evaporation process, a second microporous layer that is made of a precious metal using essentially the same evaporation angle ($\alpha$) between the substrate's surface and the evaporation source as used in forming the first microporous layer.

2. The method of claim 1, wherein the evaporation angle ($\alpha$) between the substrate's surface and the evaporation source possesses a value of from 5° to 30°.

3. The method of claim 1, wherein the precious metal is selected from the group consisting of gold, silver, palladium and platinum.

4. The method of claim 1, wherein the first microporous layer is made of a self-oxidizing metal.

5. The method of claim 4, wherein the self-oxidizing metal is selected from the group consisting of chromium, titanium and nickel.

6. The method of claim 1, wherein the precious metal is selected from the group consisting of gold, silver, palladium and platinum, and the first microporous layer is made of a self-oxidizing metal.

7. The method of claim 1, wherein the precious metal is selected from the group consisting of gold, silver, palladium and platinum, and the first microporous layer is made of a self-oxidizing metal selected from the group consisting of chromium, titanium and nickel.

8. The method of claim 1, wherein the evaporation angle ($\alpha$) between the substrate's surface and the evaporation source is set to a value that results in said microporous layers having micropores therein that possess a pore size of less than 30 nanometers.

9. A microporous, gas permeable electrode structure prepared according to the process of claim 1.

10. A microporous gas permeable electrode, comprising:

a substrate having formed thereon a first microporous gas permeable electrode layer, and formed on said first microporous gas permeable electrode layer a second microporous gas permeable layer made of a precious metal.

11. The microporous gas permeable electrode of claim 10, wherein the precious metal is selected from the group consisting of gold, silver, palladium and platinum.

12. The microporous gas permeable electrode according to claim 10, wherein the first microporous gas permeable electrode layer is made of a self-oxidizing metal.

13. The microporous gas permeable electrode according to claim 10, wherein the self-oxidizing metal is selected from the group consisting of chromium, titanium and nickel.

14. The microporous gas permeable electrode according to claim 10, wherein the precious metal is selected from the group consisting of gold, silver, palladium and platinum, and the first microporous gas permeable layer is made of a self-oxidizing metal.

15. The microporous gas permeable electrode according to claim 10, wherein the precious metal is selected from the group consisting of gold, silver, palladium and platinum, and the first microporous gas permeable layer is made of a self-oxidizing metal selected from the group consisting of chromium, titanium and nickel.

16. The microporous gas permeable electrode according to claim 10, wherein said microporous gas permeable layers have micropores therein that possess a pore size of less than 30 nanometers.

* * * * *